(12) United States Patent
Suh et al.

(10) Patent No.: US 7,491,062 B2
(45) Date of Patent: Feb. 17, 2009

(54) METHOD FOR EDUCATING A CAREGIVER ABOUT BABY CARE AND DEVELOPMENT

(75) Inventors: Mickey J. Suh, Anderson Township, OH (US); Mara Ines Rodriguez, Cincinnati, OH (US); Peter James Borowski, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 347 days.

(21) Appl. No.: 10/918,632

(22) Filed: Aug. 13, 2004

(65) Prior Publication Data

US 2006/0036224 A1 Feb. 16, 2006

(51) Int. Cl.
G09B 19/00 (2006.01)
(52) U.S. Cl. ..................................... 434/236
(58) Field of Classification Search ................. 434/236, 434/238, 247, 258, 260, 262, 219; 206/570; 446/295, 296
See application file for complete search history.

(56) References Cited

U.S. PATENT DOCUMENTS

| | | | |
|---|---|---|---|
| 3,860,003 A | 1/1975 | Buell | |
| 3,982,659 A | 9/1976 | Ross | |
| 4,154,323 A | 5/1979 | Sneider | |
| 4,185,754 A | 1/1980 | Julius | |
| 4,636,207 A | 1/1987 | Buell | |
| 4,695,278 A | 9/1987 | Lawson | |
| 4,704,115 A | 11/1987 | Buell | |
| 4,732,797 A | 3/1988 | Johnson et al. | |
| 4,741,944 A | 5/1988 | Jackson et al. | |
| 4,772,501 A | 9/1988 | Johnson et al. | |
| 4,795,454 A | 1/1989 | Dragoo | |
| 4,848,588 A * | 7/1989 | Rasmussen | 206/581 |
| 4,865,221 A | 9/1989 | Jackson et al. | |
| 4,900,317 A | 2/1990 | Buell | |
| 4,904,524 A | 2/1990 | Yoh | |
| 4,909,803 A | 3/1990 | Aziz et al. | |
| 4,940,464 A | 7/1990 | Van Gompel et al. | |
| 5,036,978 A * | 8/1991 | Frank et al. | 206/494 |
| 5,050,742 A | 9/1991 | Muckenfuhs | |
| 5,054,619 A | 10/1991 | Muckenfuhs | |
| 5,085,654 A | 2/1992 | Buell | |
| 5,092,861 A | 3/1992 | Nomura et al. | |
| 5,096,424 A * | 3/1992 | Carlberg | 434/262 |
| 5,213,254 A * | 5/1993 | Regis et al. | 229/103 |
| 5,230,450 A | 7/1993 | Mahvi et al. | |
| 5,246,433 A | 9/1993 | Hasse et al. | |
| D341,027 S | 11/1993 | Godden et al. | |

(Continued)

FOREIGN PATENT DOCUMENTS

EP 0 744 357 A1 11/1996

Primary Examiner—Kurt Fernstrom
(74) Attorney, Agent, or Firm—Charles R. Matson; Eric T. Addington; Matthew P. Fitzpatrick

(57) ABSTRACT

A method of educating a caregiver about baby care and development, wherein said method comprises the steps of preparing a self-contained baby care kit comprising a storage case, said case being suited for an initial use of storing at least one baby care product and a subsequent use of storing at least one subsequent item, at least one baby care product, and at least one educational insert; providing said self-contained baby care kit to a caregiver; and allowing the caregiver to use said kit.

17 Claims, 4 Drawing Sheets

U.S. PATENT DOCUMENTS

| | | | |
|---|---|---|---|
| RE34,920 E | 4/1995 | Aziz et al. | |
| 5,409,105 A | 4/1995 | Appelbaum et al. | |
| 5,443,161 A * | 8/1995 | Jonese | 206/581 |
| 5,492,751 A | 2/1996 | Butt, Sr. et al. | |
| 5,509,808 A * | 4/1996 | Bell | 434/247 |
| 5,531,325 A | 7/1996 | Deflander et al. | |
| 5,569,234 A | 10/1996 | Buell et al. | |
| H1630 H | 1/1997 | Roe et al. | |
| 5,629,081 A | 5/1997 | Richards et al. | |
| 5,638,957 A | 6/1997 | Brasier | |
| 5,648,083 A | 7/1997 | Blieszner et al. | |
| 5,690,495 A * | 11/1997 | Collier | 434/258 |
| 5,725,382 A * | 3/1998 | Walter et al. | 434/258 |
| 5,813,558 A | 9/1998 | Burke | |
| 5,863,663 A | 1/1999 | Mackey et al. | |
| 5,871,763 A | 2/1999 | Luu et al. | |
| 5,897,545 A | 4/1999 | Kline et al. | |
| 5,924,572 A * | 7/1999 | Cope | 206/518 |
| 5,934,470 A | 8/1999 | Bauer et al. | |
| 5,950,834 A * | 9/1999 | Woodnorth et al. | 206/541 |
| 5,957,908 A | 9/1999 | Kline et al. | |
| 5,996,749 A * | 12/1999 | Hillsberg et al. | 190/109 |
| 6,060,149 A | 5/2000 | Nissing et al. | |
| 6,082,545 A * | 7/2000 | Ford et al. | 206/579 |
| 6,083,854 A | 7/2000 | Bogdanski et al. | |
| 6,092,690 A | 7/2000 | Bitowft et al. | |
| 6,120,487 A | 9/2000 | Ashton | |
| 6,120,489 A | 9/2000 | Johnson et al. | |
| 6,269,970 B1 | 8/2001 | Huang et al. | |
| 6,390,260 B1 | 5/2002 | Roegner | |
| 6,476,288 B1 | 11/2002 | VanRijswijck et al. | |
| 6,523,690 B1 | 2/2003 | Buck et al. | |
| 6,537,074 B2 * | 3/2003 | Jurmain et al. | 434/238 |
| 6,550,634 B1 | 4/2003 | Alegre De Miquel et al. | |
| 6,604,651 B2 | 8/2003 | Amundson et al. | |
| 6,623,834 B1 | 9/2003 | Nissing et al. | |
| 6,648,864 B2 | 11/2003 | Ronn et al. | |
| 6,723,080 B1 * | 4/2004 | Habib et al. | 604/385.06 |
| 6,733,773 B1 | 5/2004 | Hsu et al. | |
| 6,745,895 B2 | 6/2004 | Silvers | |
| 2002/0050503 A1 | 5/2002 | Spero | |
| 2003/0118975 A1 * | 6/2003 | Stamm et al. | 434/236 |
| 2003/0152896 A1 * | 8/2003 | Hudson | 434/258 |
| 2003/0233082 A1 | 12/2003 | Kline et al. | |
| 2004/0048229 A1 * | 3/2004 | Thurman | 434/237 |
| 2005/0008681 A1 | 1/2005 | Deckner | |
| 2005/0173292 A1 * | 8/2005 | Klose et al. | 206/581 |
| 2005/0241985 A1 * | 11/2005 | Mosbacher et al. | 206/570 |
| 2006/0032782 A1 | 2/2006 | Suh et al. | |

* cited by examiner

US 7,491,062 B2

METHOD FOR EDUCATING A CAREGIVER ABOUT BABY CARE AND DEVELOPMENT

FIELD OF THE INVENTION

The present invention relates to a self-contained baby care kit that includes a case having a subsequent use. The self-contained baby care kit is particularly useful for babies that wear diapers and like absorbent articles.

BACKGROUND OF THE INVENTION

The birth of a child is often one of the most important and joyous moments in the life of a parent. The joy a parent may have with the birth of a child may be tempered by significant stress and anxiety, especially for first-time parents who have not developed the skills necessary to care for a newborn baby. Parents are often confused about basic baby care topics such as feeding, hygiene, and development. Adding to this confusion is an overload of information received by means such as promotions, samples, offers, pamphlets, books, television, and other routes of communication. By combining the parents' own confusion about baby care along with the information overload they experience, parents often will make care decision based on necessity rather than upon analysis of the information received.

Manufacturers of products designed for babies often conduct extensive research involving the growth and development of babies in order to design better products. Consequently, these manufacturers have valuable and useful information regarding babies and young children. This information may include topics such as baby characteristics, development patterns, and the like. Practical education and advice may also be provided in light of the extensive research on baby growth and development. Such practical education and advice may include tips on baby care, feeding, health, hygiene, and the like. The problem for manufactures of baby products is conveying their extensive research and insight to parents.

Manufacturers of baby products have tried to implement a variety of strategies to convey their extensive information and knowledge in a way that will be useful, engaging, and informative to parents. One commonly used way of conveying information is by providing the parent with information at critical points in the baby's life or care needs. For example, parents are often provided with information related to newborn care while at a birth facility and, especially, while at the birth facility for the purpose of delivery. Unfortunately, as more manufacturers of baby care products provide more information to parents while at the birth facility, information of higher value to the parents tends to be lost in the information overload. Thus, it is advantageous for manufacturers of baby care products to distinguish their information, knowledge, and products from those typically distributed to parents.

One mechanism manufacturers of baby care products use to convey their information and products is by providing samples of relevant newborn care products such as diapers, wipes, formula, ointments, and the like. Samples of items such as diapers and wipes tend to be limited in number, and, as a result, offer limited opportunity for the parents to explore and learn about the product. A sample package containing 1 or 2 diapers generally will not allow the parents to explore the unique benefits provided by the diaper. Furthermore, for some first-time parents this may be the first time they have ever applied a diaper. These parents may need to apply several diapers before they feel comfortable with diapering. A sample package containing a small quantity of diapers may not be sufficient.

Manufacturers of baby care products have not been completely successful in delivering information that encourages the parents to use the information over a prolonged period of time. Educational pamphlets, mailings, and fliers are often discarded. Delivery of information by mass media is often forgotten and not easily retrievable. Sample products are used and discarded.

In light of the above identified deficiencies, the present invention provides a method for conveying an informative message to parents over a prolonged period of time. Specifically, the present invention is directed to a method of educating a caregiver about baby care and development with the steps of preparing a self-contained baby care kit, providing said self-contained baby care kit to a caregiver; and allowing the caregiver to use said kit.

SUMMARY OF THE INVENTION

The present invention relates to a method of educating a caregiver about baby care and development, wherein said method comprises the steps of preparing a self-contained baby care kit comprising a storage case, said case being suited for an initial use of storing at least one baby care product and a subsequent use of storing at least one subsequent item, at least one baby care product, and at least one educational insert; providing said self-contained baby care kit to a caregiver; and allowing the caregiver to use said kit. In one embodiment, the baby care product can include diapers and/or wipes. In one embodiment, the subsequent item is a baby related memento.

DETAILED DESCRIPTION OF THE INVENTION

As used herein, the term "absorbent article" refers to devices which absorb and contain body exudates and, more specifically, refers to devices which are placed against or in proximity to the body of the wearer to absorb and contain the various exudates discharged from the body. The term "absorbent article" includes devices such as incontinence briefs, incontinence undergarments, absorbent inserts, pant type garments (e.g., pants are also commonly referred to as "closed diapers", "prefastened diapers", "pull-on diapers", "training pants," and "diaper-pants"), diaper holders and liners.

As used herein, the term "disposable" describes absorbent articles which generally are not intended to be laundered or otherwise restored or reused as absorbent articles (i.e., they are intended to be discarded after a single use and, preferably, to be recycled, composted or otherwise discarded in an environmentally compatible manner.

As used herein, the term "stages of development" or "developmental stage" refers to the level of emotional and cognitive maturity and/or the physical abilities of an individual of a baby and includes locomotion, mobility, motor skills, and coordination.

As used herein, the term "baby-related memento" means any item that is saved as a reminder of a baby's past. Generally, such items are saved by a caregiver and more specifically a parent. Baby-related mementos may include for example photographs, birth certificates, hand imprints, foot imprints, clothing, locks of hair, hospital wrist bands, caregiver notes or reflections, booties, hat, and the like.

As used herein, the term "caregiver" refers to a person is responsible for the care needs of a baby. Generally, the caregiver is the person who is responsible for the diaper changing needs of the baby. The caregiver can include for example a parent, a grandparent, any relative, a babysitter, a nanny, a preschool teacher, and the like. The caregiver is the person most likely to interact with the kit of the present invention.

As used herein, the term "baby" refers to a child who still wears an absorbent article to absorb and contain the various exudates at the rate of at least one per week. The term "baby-"may include for example newborn, premature babies, infants, toddlers, and incontinent children.

As used herein, the term "graphic" refers to any design, pattern, or the like that is or becomes visible and specifically includes text messages that consist of one or more alphanumeric symbols, pictorial images that consist of one or more pictures, and combinations thereof.

Figure 1:
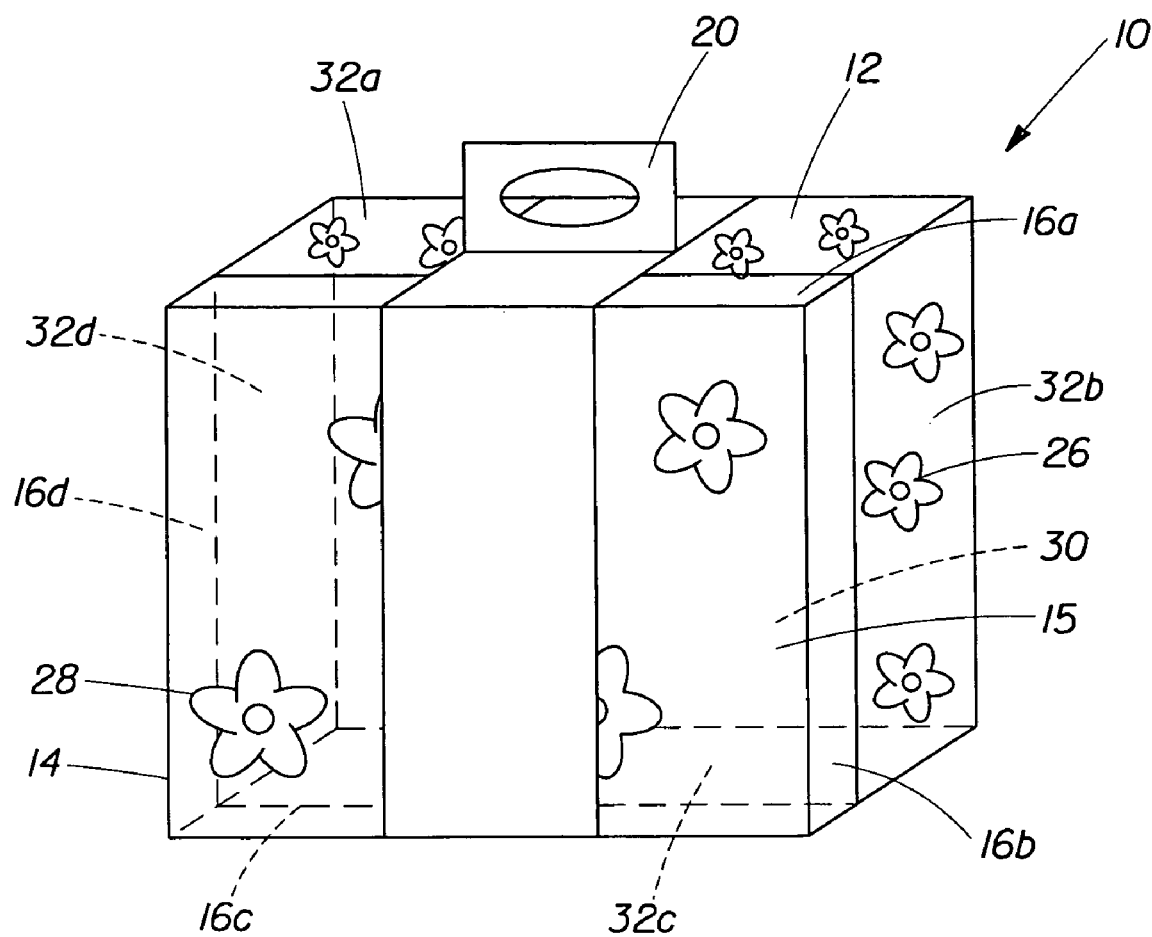
FIG. 1 is a perspective view of one embodiment of a self-contained baby care kit shown as it may be carried.
Figure 2:
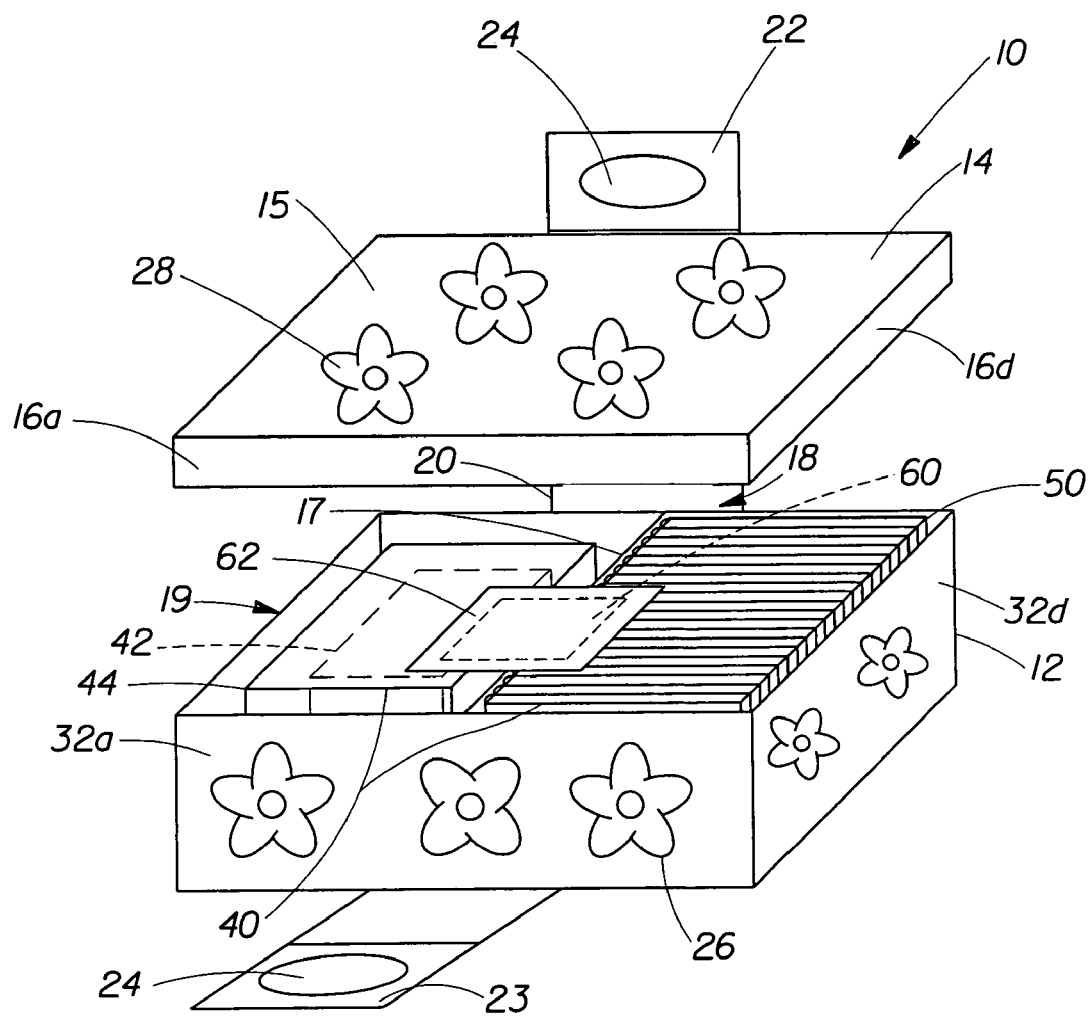
FIG. 2 is an exploded view of one embodiment of a self-contained baby care kit shown as it may be used.

FIG. 1 is a perspective view of a self-contained baby care kit 10 having a subsequent use. Generally, as shown in FIG. 1, the kit 10 may include a storage case 12 that has an initial use for storing at least one baby care product and a subsequent use for storing a subsequent item. The subsequent item can be any item that may be contained within the case 12. The subsequent item may be of the caregivers choosing but suggestions as to items that may by subsequently stored may be provided. In one embodiment, the kit 10 has the subsequent use of storing one or more baby-related mementos. The kit 10 may comprise a lid 14 that releasably engages the storage case 12. The kit 10 may also have a carrying handle 20. The storage case 12 may be any type of container that may initially store one or more baby care products and may subsequently be used to store one or more baby-related mementos. FIG. 2 is an exploded view of the kit 10 of FIG. 1 with the handle 20 and lid 14 being disengaged from the case 12. FIG. 2 is an exploded view showing the kit 10 of FIG. 1.

In the one embodiment shown in FIG. 1, the case 12 is shown as being a hexahedral solid, i.e., a three-dimensional figure having length, width, and depth and comprising six quadrilateral faces. The case 12 may have a bottom wall 30 joined to four sidewalls 32a-d to form an interior space 18 (as shown is FIG. 2) of the storage case 12. The lid 14 may form the sixth face of the storage case 12. While the dimensions of the storage case 12 are not to be read as limiting, the case 12 may have an interior space 18 of sufficient size so as to house at least one baby-care product and, in it subsequent use, a baby-related memento. In certain embodiments, the case 12 is sized such that, in its initial use of storing a baby-care product, unoccupied space (i.e., space not occupied by the baby-care product) is kept to a minimum. The hexahedral shape and size of the case 12 are beneficial in that they allow for storage of one or more baby care products and subsequent storage of one or more baby care mementos while still allowing for easy palletization, transport, and delivery. However, one would clearly recognize that the shape of the storage case 12 is not limited to the hexahedral shape as shown in FIG. 1. The storage case 12 may alternately be of any other shape provided that the case 12 allows for storage of both a baby-care product and, in its subsequent use, a baby-related memento. For example, there may be five sidewalls so that that case 12 is a prism having pentagon-shaped base.

As shown in FIG. 2, the case 12 may have one or more dividers 17. The divider 17 allows for further compartmentalization of the interior space 18 of the case 12. The divider 17 may be made of the same materials as the case 12. The divider 17 may be affixed to the case 12 or may be removable so that a caregiver can customize the case 12 for the subsequent use of storing baby-related mementos. The divider 17 may be positioned so that each baby care product 40 is housed within a compartment. The divider 17 may also be positioned to optimize space in the subsequent storage of baby-related mementos. In the embodiment shown in FIG. 2, the divider 17 spans substantially the entire width and depth of the case 12 and divides the case into two compartments with approximately the same dimensions.

Being that the storage case 12 has an initial and subsequent use, the case 12 may be constructed of a relatively durable material. Examples of such durable materials include paperboard, cardboard, corrugated cardboard, plastic, synthetic materials, and other sufficiently durable and rigid material.

The storage case 12 may include a graphic 26, ideally on an exterior surface of the case 12. The graphic 26 may by colored or multi-colored. The graphic 26 may be a customizable graphic that allows for personalization of the graphic 26 by the caregiver. Customizable graphics may include graphics that can be altered by the caregiver by means of coloring, writing, stamping, stickering, or the like. In one embodiment, the customizable graphic may include a graphic that allows the caregiver to write in personalized information like a baby's name, date of birth, time of birth, eye color, weight, length, and the like.

The case 12 may have a lid 14. The lid 14, as shown in FIG. 1, is in a closed position such that the lid 14 along with the bottom wall 30, and side walls 32a-d provide a partial or full physical boundary to the interior space 18 of the case 12. The lid 14 may reversibly engage the storage case 12 so as to allow access to the interior space 18 through a case opening 19. The lid 14 may include a top surface 15 and four flanges 16a-d extending downwardly from the top surface 15. In the closed position, the lid 14 engages the case 12 such that the flanges 16a-d overlap the sidewalls 32a-d in a one-to-one relationship. The top surface 16 may substantially serve as the sixth surface of the hexahedral-shaped case 12. As shown in FIG. 2, the lid 14 is in an open position being disengaged from the case 12. With the lid 14 in the open position, the interior space 18 of the case 12 is now accessible through the case opening 19. As shown, the lid 14 may be a structure separate from the case 12.

In another embodiment, the lid 14 may be integral to the case 12 such that lid 14 is attached to the case 12. For example, the lid 14 may be hingedly attached to one of the side walls 32 of the case 12. The hingely attached lid 14 can be provided in any manner well-known in the art such as forming the case 12 from a single piece of material that is cut and folded into a hexahedral shape. In another example, the lid 14 could be cut and folded such that one flange 16 is hingedly attached top surface 15 of the lid 14. The hinged flange 16 may then be affixed to the sidewall 32 of the case 12 by any means known in the art.

The lid 14 may be sized such that it substantially covers the case opening 19. While the dimensions of the lid are not to be read as limiting, generally, the lid 14 may be sized in fit snugly on the case 12. The lid 14 may be constructed of a relatively durable material such as paperboard, cardboard, corrugated cardboard, plastic, synthetic materials, and other sufficiently durable and rigid material. Generally, the lid 14 is constructed of the same material as the case 12. In some embodiments of the present invention, the kit 10 may omit the lid 14.

The lid 14 may include a lid graphic 28. The lid graphic 28 may by colored or multi-colored. The lid graphic 28 may be a customizable graphic that allows for personalization of the lid graphic 28 by the caregiver. Customizable graphics may include graphics may be altered by the caregiver by means of coloring, writing, stamping, stickering, or the like. In one embodiment, the customizable graphic may include a graphic that allows the caregiver to write in personalized information like a baby's name, date of birth, time of birth, eye color, weight, length, and the like. The lid graphic 28 may be similar to the graphic 26.

The case 12 and/or the lid 14 may include a window allowing the caregiver to visually perceive the contents of the kit 10 without opening the case and/or removing the lid. Within the context of this description, the contents are visually perceivable if the window is capable of transmitting light and an observer can discern the contents of the case 12 and/or lid 14. The window may be a cut-out from the case 12 and/or lid 14, wherein the material from which the case 12 and/or lid 14 is constructed is removed, omitted, or removable. The window may be made from a substantially transparent material such that the contents therein may be seen and discerned by the caregiver. A suitable transparent material may be a polyethylene film or film laminate such as a low density polyethylene (LDPE) film, a LDPE/ linear low density polyethylene (LLDPE) film laminate, a LDPE/ medium density polyethylene (MDPE) film laminate, a LDPE/ high density polyethylene (HDPE) film laminate or the like.

The handle 20 may be provided to aid in transport of the kit 10 by the caregiver. As shown in FIG. 2, the handle 20 may be an overwrap structure that at least encircles a part of the case 12. The handle 20 may be substantially rectangular in shape, as shown; however, the shape of the handle may be varied. The handle may comprise two distal surfaces 22, 23. The distal surfaces 22, 23 may each comprise an aperture 24 that serves as a grasp-point for the caregiver. The handle 20 may be positioned encircling the case 12 such that the two distal surfaces 22, 23 are placed in a face-to-face relationship with one another so that the apertures 24 are aligned. The handle 20 may be permanently or detachably affixed to the case 12. For example, the handle 20 may be a discrete structure that is affixed to the case 12 by means well-known in the art such as by an adhesive. In another embodiment, the handle 20 may be integral to the case 12. For example, the handle 20 can be provided in the process of forming the case 12 from a single piece of material that is cut and folded to provide the case 12 as well as the handle 20. The handle 20 may be constructed from a variety materials such as paperboard, cardboard, corrugated cardboard, plastic, synthetic materials such as polymeric films, and other sufficiently durable and rigid material.

Figure 3:
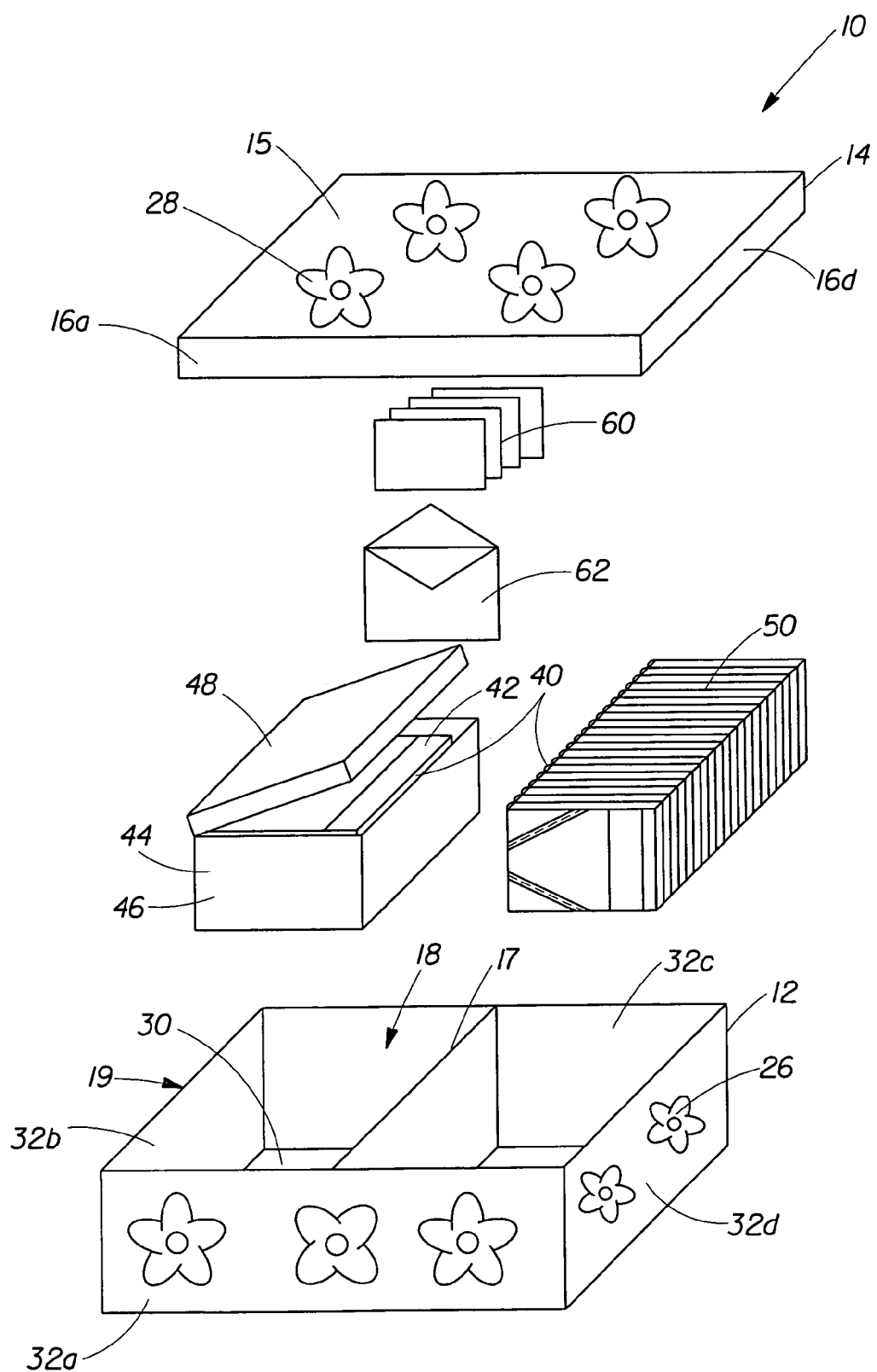
FIG. 3 is an exploded view of one embodiment of a self-contained baby care kit showing the contents of this one embodiment.

FIG. 3 is an exploded view of one embodiment of the kit 10 of the present invention showing the contents of the kit 10 of FIG. 2 without the handle 20. The interior space 18 of the case 12 is shown housing at least one baby care product 40 (shown as a plurality of wipes 42 enclosed within a container 44 and a plurality of absorbent articles such as diapers 50). The interior space 18 of the case 12 is also shown to house an educational insert 60.

The kit 10 comprises at least one baby care product 40. The baby care product 40 may be any item that is predominately used for baby care including items related to hygiene, feeding, safety, health, and the like. Baby care products 40 may include absorbent articles (e.g., diapers, pants, and the like), wipes, powders, ointments, medications, hair brushes, bottles, pacifiers, wash cloths, towels, sanitizers, soap, baby wash, baby shampoo, baby lotion, sponges, bibs, eye drops, nasal aspirators, thermometers, changing pads, diaper disposal bags, and the like. The baby care products 40 included in the kit 10 may be targeted for a particular baby care purpose such as feeding, bathing, changing, nurturing, and the like or can include a mixture of baby care products 40 for different purposes. For example, baby care products 40 targeted to changing could include diapers, wipes, diaper rash ointment, hand sanitizers, changing pads, disposal bags, and the like. In the embodiment shown in FIG. 3, the baby care products 40 include wipes 42 and diapers 50.

The kit 10 may contain one or more absorbent articles such as disposable diapers 50. Diapers 50 and like disposable absorbent articles are well-known in the art. Exemplary diaper construction is detailed in U.S. Pat. Nos. 3,860,003; 4,636,207; 4,695,278; 4,704,115; 4,795,454; 4,900,317; 4,909,803 (Reissued as U.S. RE34920); U.S. Pat. Nos. 5,085,654; 5,492,751; 6,476,288; and SIR H1630. Exemplary pants construction is disclosed in U.S. Pat. Nos. 5,246,433; 5,569,234; 6,120,487; 6,120,489; 4,940,464; 5,092,861; 5,897,545; 5,957,908; and U.S. patent application Ser. No. 10/171,249.

In one embodiment, the kit 10 may contain more than one diaper 50. In other embodiments, the kit 10 may contain ten (10) or more diapers 50. The kit 10 may contain twenty (20) or more diapers 50. The kit 10 preferably contains a sufficient number of diapers 50 to allow the caregiver to have prolonged contact time with the diapers 50. The prolonged contact time means that a sufficient number of diapers 50 are provided to allow for multi-day use of the diapers 50. By providing a caregiver with a sufficient number of diapers 50, the caregiver can learn by doing; namely, the caregiver can learn the unique features of the diapers 50 by being given several of the diapers 50 to use. Furthermore, by providing a sufficient number of diapers, the caregiver is educated as to how the diapers 50 perform over a variety of wear conditions. For example, diapers 50 are more likely to be more heavily loaded with bodily exudates during overnight wear when changes are less frequent. During daytime wear, diapers 50 experience increased stress related to baby activity and motion. Providing a sufficient number of diapers 50 will help the caregiver learn about the performance characteristics of the diaper under such differing wear conditions.

The diapers 50 contained within the kit 10 may be designed for any size baby. Different sized diapers 50 may be provided within the kit 10. Typically, diapers 50 are sized according to the weight of the baby. An exemplary range of sizes could include 0-10 lbs (0-4.5 kg), 8-14 lbs (4-6 kg), 12-18 lbs (5-8 kg), 16-28 lbs (7-13 kg), 22-37 lbs (10-17 kg), 27 or more lbs (12+kg), and 35 or more lbs (16+kg). Such ranges could be qualitatively labeled as newborn, size 1, size 2, size 3, size 4, size 5, and size 6, respectively. Such ranges are typically provided as a guide to parents as to what diaper will best fit what baby, and it should be noted that a baby of a certain weight may wear a diaper with a size-range not covering said baby's weight. In one embodiment of the invention, the kit 10 contains newborn-size diapers. Such a kit 10 containing newborn diapers 50 would be advantageous for caregivers with a newborn baby.

The diapers 50 may be packaged as a self-contained unit. The self-contained unit results in a plurality of diapers 50 being bound to one another in order to improve delivery and handling. In one embodiment, the self-contained unit is defined by numerous diapers 50 bound together as an entity and covered by a thermoplastic film overwrap as disclosed in U.S. Pat. No. 5,934,470 issued to Bauer et al. on Aug. 10, 1999. Other means of achieving a self-contained unit are clearly envisioned. For example, the overwrap may comprise a variety of materials including, but not limited to, thermoplastic films, nonwovens, wovens, foils, fabrics, papers, cardboard, elastics, cords, straps, and combinations thereof. The overwrap may completely or partially bind and/or cover the plurality of diapers 50. Other suitable packages and methods for packaging are disclosed in U.S. Pat. No. 5,050,742 issued to D. R. Muckenfuhs on Sep. 24, 1991; and U.S. Pat. No. 5,054,619 issued to D. R. Muckenfuhs on Oct. 8, 1991. Furthermore, the self-contained unit may contain multiple overwraps. For example, a plurality of diapers 50 may be packaged with a thermoplastic film overwrap and then a plurality of film wrapped diaper being overwrapped in a cardboard box or a second thermoplastic film overwrap.

The overwrap may contain a window which allows the caregiver to visually perceive the diapers 50 within the overwrap without opening or breaching the overwrap. Within the context of this description, the diapers 50 are visually perceivable if the window is capable of transmitting light and an observer can discern the contents within the overwrap. The window may be a cut-out from the overwrap, wherein the material from which the overwrap is constructed is removed, omitted, or removable. The window may be made from a substantially transparent material such that the diapers 50 within the overwrap may be seen and discerned by the caregiver. A suitable transparent material may be a polyethylene film or film laminate such as a low density polyethylene (LDPE) film, a LDPE/ linear low density polyethylene (LLDPE) film laminate, a LDPE/ medium density polyethylene (MDPE) film laminate, a LDPE/ high density polyethylene (HDPE) film laminate or the like. In one embodiment, the window of the overwrap is positioned in proximity to the window of the case 12 and/or lid 14 such that the diapers 50 may be discerned by the caregiver without opening the case 12, lid 14, and/or overwrap.

In another embodiment, the self-contained unit may contain an opening means to allow access to the diapers 50. The kit 10 may require activation so that the article becomes accessible (e.g., opening of a lid, removal of a panel, etc.). A typical opening means includes a substantially continuous line of weakness such as perforations within the thermoplastic film overwrap. An exemplary opening means is presented in U.S. patent application No. 5,036,978 issued to Frank et al. on Aug. 6, 1991. The self-contained unit may omit a dedicated opening or cutting means. For example, a thermoplastic film overwrap without perforation may be opened by tearing the film thereby accessing the diapers 50.

The kit 10 may contain one or more wipes 42. Wipes 42 are well-known in the art and may also be referred to as wet wipes, dry wipe, pre-moistened wipes, towelettes, and the like. Wipes 42 are commonly used to clean the anus, the perineum, the perianal and perineal area, and external genitalia after defecation or urination. Wipes 42 are particularly useful and frequently used for cleansing during diaper changes. Wipes 42 may be made of a material impregnated with a liquid or semi-liquid composition. The material of the wipes 42 is generally soft and flexible.

The material may have relatively high values of texture, caliper, and bulk for increased absorbency and cleansing. The liquid or semi-liquid composition impregnated into the wipe may enhance cleansing, skin softness, and/or skin condition. Exemplary wipe construction is detailed in U.S. Pat. Nos. 4,732,797; 4,741,944; 4,772,501; 4,865,221; 4,904,524; 5,629,081; 5,648,083; 5,863,663; 5,871,763; 6,060,149; 6,083,854; 6,623,834; and 6,733,773. Exemplary wipe construction is also detailed in U.S. application Ser. No. 10/883,314 entitled "Composition for Wet Wipes that Enhances the Efficacy of Cleansing While Being Gentle to the Skin" filed Jul. 1, 2004 in the name of G. E. Deckner et al.

In one embodiment, the kit 10 may contain more than one wipe 42. The kit 10 may contain twenty (20) or more wipes 42. In another embodiment, the kit 10 may contain forty (40) or more wipes 42. The kit 10 preferably contains a sufficient number of wipes 42 to allow the caregiver to have prolonged contact time with wipes 42. The prolonged contact time means that a sufficient number of wipes 42 is provided to allow for multi-day use of the wipes 42. It is believed that caregivers gain a better understanding of a product given increased contact time with said product. By providing a caregiver with a sufficient number of wipes 42, the caregiver can learn by doing; namely, the caregiver can learn the unique features of the wipes 42 by being given several wipes to use.

The wipes 42 may be packaged in a container 44. The container 44 provides a means of enclosing the wipes 42 in order to improve handling and delivery. Enclosing the wipes 42 in the container 44 also prevents the liquid or semi-liquid composition impregnated into the wipe from evaporating or otherwise dissociating from the wipe. The container 44 may be made from a rigid or flexible material. In one embodiment, the container 44 is made from any suitable plastic material. Suitable plastics include polypropylene, polyethylene, polystyrene, acrylonitryl butadiene styrene, polyester, polyvinyl chloride, polycarbonate and high density polyethylene.

The container 44 may be provided in any shape such as a cuboid, rectangular solid, cylinder and the like. In one embodiment, the container 44 is a rectangular solid and may be made of a body and a lid. The container body 46 may form an interior space in which one or more wipes 42 may be housed and a container opening. The container opening allows the caregiver to access the wipes 42. The container 44 may further include a container lid 48. The container lid 48 is typically mounted onto the container body 46 and may be affixed thereto by means of threads, snap fittings, interengaging ribs, frictional engagements, adhesives and the like. The container lid 48 may be attached to the container body 46 by a hinge mechanism such as is shown in U.S. Pat. No. 6,092,690. The container lid 48 may engage the container body 46 such that, in a closed position, the container lid 48 covers and/or seals the container opening. However, the container lid 48 may be removable from the container body 46. The container 44 may form a moisture impervious seal thereby preventing desiccation of the wipes 42 housed in the container body 46. Exemplary containers are further described in U.S. Pat. Nos. 6,523,690; 6,550,634; 6,269,970; and 5,531,325. The container lid 48 may be sized so as to allow for a second plurality of wipes to be inserted into the container 42 (i.e., a refillable container).

The wipes 42 may be packaged within a wrapper. The wrapper may be made from a moisture impervious, non-rigid material such as polymer films, metallic foils, and the like. Wipes 42 packaged within a wrapper are commonly used to refill rigid containers; however, the wrapper may include a recloseable dispensing mean allowing access and removal of one or more wipes 42. Exemplary non-rigid containers with recloseable dispensing means are described in U.S. Pat. Nos. 6,604,651; 4,185,754; 3,982,659; and European Patent Application No. EP0744357A1 entitled "Package for tissues comprising a flexible pouch and a re-usable dispensing device."

The wrapper may contain a window which allows the caregiver to visually perceive the wipes 42 within the wrapper without opening or breaching the wrapper. Within the context of this description, the wipes 42 are visually perceivable if the window is capable of transmitting light and an observer can discern the contents within the wrapper. The window may be made from a substantially transparent material such that the wipes 42 within the wrapper may be seen and discerned by the caregiver. A suitable transparent material may be a polyethylene film or film laminate such as a low density polyethylene (LDPE) film, a LDPE/ linear low density polyethylene (LLDPE) film laminate, a LDPE/ medium density polyethylene (MDPE) film laminate, a LDPE/ high density polyethylene (HDPE) film laminate or the like. In one embodiment, the window of the wrapper is positioned in proximity to the window of the case 12 and/or lid 14 such that the wipes 42 may be discerned by the caregiver without opening the case 12, lid 14, and/or wrapper.

The case 12 may contain one or more educational inserts 60. The educational inserts 60 may provide or offer to provide information, instruction, tips, advice, directions, coaching, guidance, or counsel. The inserts are may be in a variety of formats including pamphlets, notecards, fliers, magazines, audio formats including compact discs, DVD discs, computer readable CDs, and the like. In one embodiment, the educational inserts 60 may be cards made from cover paper or card stock and printed with the relevant information. These cards may have a substantially rectangular shape although one or more sides may be curvilinear. While the card may be of any dimension, a suitable dimension is approximately 6 inches (15.2 cm) by 4 inches (10.2 cm). The educational inserts 60 may be contained within an envelope 62 or other like structure that can keep a plurality of inserts 60 bound together at least during the initial use of the case 12 for storing the baby care product 40.

One of the educational inserts 60 may be a subsequent use insert that provides instruction regarding the subsequent use of the case 12 for storing a subsequent item such as a baby related memento. The subsequent use insert may inform the caregiver that the case 12 has a secondary use beyond that of storing and housing the one or more baby care products 40. The subsequent use insert may provide ideas as to what types of mementos a caregiver should keep such as photographs, birth certificates, hand imprints, foot imprints, locks of hair, hospital wrist bands, caregiver notes or reflections, clothing, booties, hats, and the like. The subsequent use insert may instruct the caregiver on how to reconfigure the case to more effectively store baby-related mementos. The subsequent use insert may also provide direction on how to effectively organize, manage, and store the mementos using the case. For example, the subsequent use insert may direct a caregiver to place one or more dividers into the case thereby allowing for compartmentalization of the mementos. The subsequent use insert may direct the caregiver to use an indexing insert as a way of categorizing the mementos. Indexing inserts may contain a generic baby-related category descriptor (e.g., "birth to 1 month"; "newborn," "baby," "toddler," etc.; "January," "February," etc.) and/or a blank area for customization by the caregiver. In one embodiment, the indexing inserts may provide little to no text. In such an embodiment, the indexing inserts may provide dedicated space for the caregiver to customize. For example, the indexing inserts may provide dedicated space in which a caregiver may insert his or her own baby-related category descriptor. Furthermore, the indexing inserts may provide dedicated space in which a caregiver can list the baby-related mementos stored relative to the indexing insert. Such an indexing insert assists in the organization of the mementos.

One of the educational inserts 60 may be a stage of development insert providing information on one or more stages of baby development. The stages of development refer to the level of emotional and cognitive maturity and/or the physical abilities of an individual of a baby including locomotion, mobility, motor skills, and coordination. The stages of development may cover a broad range of baby development. An exemplary range is from newborn to active toddler and includes five developmental stages: pre-locomotive, discovering, exploring, learning, and training. A first stage of development might cover a pre-locomotive phase and include newborns who are in a bonding stage with the caregiver and other immobile infants whose level of activity might include little more than head raising or rolling over. A second stage of development might cover a discovering stage comprising a crawling phase and include curious toddlers exhibiting developing activity in the form of sitting and mobility in the form of scooting, rolling and crawling. A third stage of development might cover an exploring stage comprising a walking phase and include toddlers whose level of activity includes standing, walking and beginning to run. A fourth stage of development might cover a learning phase and include toddlers capable of doing things by themselves such as dressing and developing coordination which enables them to walk and run without losing balance. A fifth stage of development might cover a training stage and include toddlers undergoing toilet training, attempting to achieve independence and overall, undergoing a transition from baby to child. Clearly, other stages are contemplated; for example, other stages may overlap or be a subset of the aforementioned stages. Further information related to stages of baby development may be found in U.S. Pat. No. 6,648,864. The stages of development may be span or include other baby stages including, but not limited to, age ranges, weight ranges, size ranges, and the like.

The information related to the stage of baby development may include developmental insights, care tips, and practical advice. Developmental insights may include information that is related to a baby's physical, behavioral, cognitive, and/or mental development. For example, developmental insights may include information explaining what physical traits to expect from the baby during each of the stages of development, advice on having more effective interactions given a baby's mental development, and on how to react to a baby's behavior. Care tips may include information related to feeding, sleeping, health, diapering, skin care, and like baby care topics. An exemplary care tip may be advice on food that is appropriate for each of the developmental stages. Practical advice may include other assorted advice relevant to the developmental stages but which is often directed more to the responsibilities and activities of the caregiver. For example, practical advice appropriate for the pre-locomotive stage of development may be information for a caregiver on how handling a baby's first photographic portrait session. Other practical advice may include such topics as recipe/meal ideas, stress-reduction advice, and dealing with holidays.

One of the educational inserts 60 may be a product information insert. The product information insert may provide information related to the baby care product 40 initially stored within the case. The product information may include information on the construction, design, materials, benefits, and other characteristics of the baby care product 40. The product information may describe one or more technical benefits of the baby care product 40. For example, technical benefits may include information regarding improved fit for a diaper, improved cleaning for a wipe, or improved absorbency of a bib. The product information may also provide preferential information related to the baby care product 40. Such information may include statements that the product is preferred, recommended, selected, or purchased by one or more individuals or groups of individuals (e.g., "The Pediatricians' Choice").

The product information may include information related to other baby care products that are not initially provided with the kit 10 or within the case 12. For example, a case initially storing a plurality of wipes and a plurality of diapers may have product information on such related products as ointments, powders, bottles, changing pads, and the like. Generally, both the baby care product initially provided with the kit 10 as well as the information on other baby care products not with the kit 10 are all manufactured, distributed, and/or sold by a common entity (e.g., a single person, corporation, group, partnership, etc.). The product information may be keyed to the stages of baby development, as disclosed above.

One of the educational inserts 60 may be an additional information insert. The additional information insert provides a means for obtaining additional baby care information. The additional information insert provides instruction on how to obtain additional information. The instruction may be filling out and submitting a postcard. The instruction may be contacting a World Wide Web site or calling a telephone number. The additional information may be provided to the caregiver by mail, telephone, e-mail, or World Wide Web page. The additional baby care information may be information related to the subsequent use of the case, to the stages of baby development, and/or to product information. The additional baby care information may also include such items as promotional item offers, additional samples, coupons, rebate offers, and the like.

Figure 4:
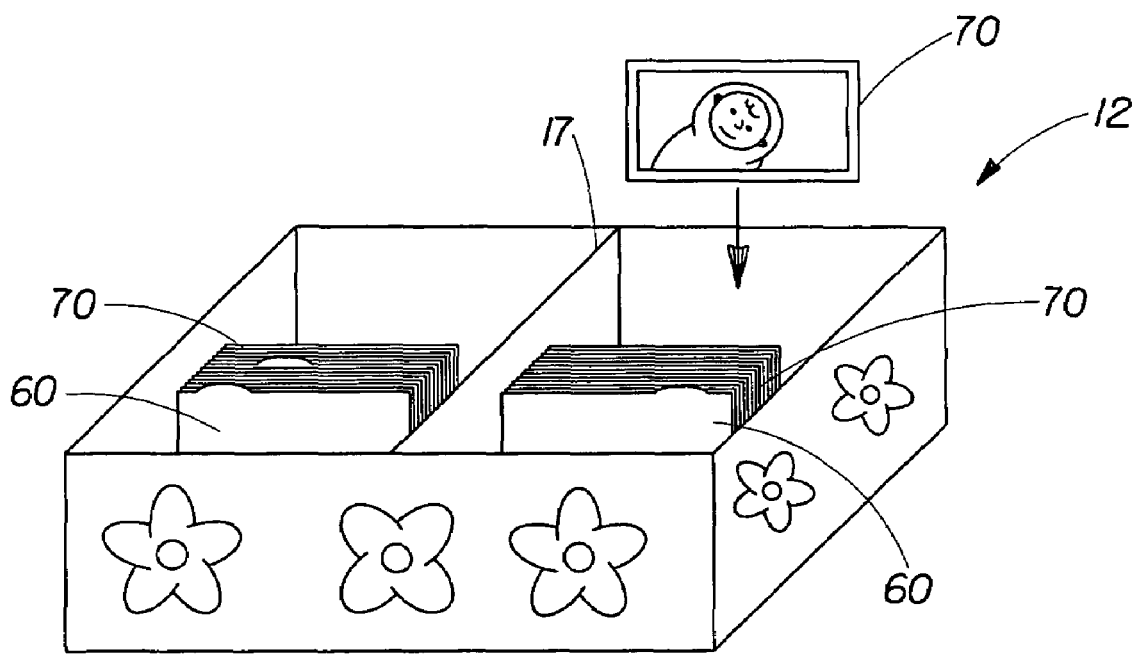
FIG. 4 is a perspective view of one embodiment of the case in its subsequent use as a photograph box.

FIG. 4 shows an embodiment of the present invention wherein the case 12, with the lid removed, is engaged in a subsequent use for storing one or more baby-related mementos. The case 12 may be used to store a plurality of photographs 70. The divider 17 may be positioned so as to maximize the space available of storing the photographs 70. As shown, the divider 17 may divide the case into two compartments each having approximately a 6" width and approximately a 4" depth so as to house common photographic print sizes. One or more of the educational inserts 60 may be used to organize the photographs 70. For example, the indexing insert may be used to organize photographs 70 according to a generic baby-related category descriptor that may be printed on the indexing insert or that may be written on to the indexing insert by the caregiver (e.g., 0-3 months, 3-6 months, etc.). Other educational inserts 60 such as stage of development insert may be included within the photographs. The stage of development insert may be placed with the indexing insert and/or photographs that overlap the particular stage of development. For example, stage of development insert directed to the prelocomotive stage may be organized along with an indexing insert and photographs that relate to this prelocomotive stage. Such organization assists in ensuring that the stage of development information conveyed by the stage of development insert is more readily accessible when needed by a caregiver.

In another embodiment, a kit 10 of the present invention may be prepared according to the disclosure present above. The kit 10 of may be provided to a caregiver so that the caregiver has an opportunity to use and interact with the kit 10. More specifically, the caregiver should be provided an opportunity to use the enclosed baby care products 40. In one embodiment, the kit 10 has a sufficient quantity of baby care product 40 to last at least 24 hours given normal use patterns. Furthermore, the caregiver should be provided an opportunity to interact with the educational insert(s) housed within the case and/or the case itself. The opportunity to interact with the case includes allowing the caregiver to use the case according to the secondary use for storing at least one baby-related memento.

While the kit 10 may be provided to the caregiver at any time, the kit 10 is preferably provided to a caregiver at a point during the baby's development most appropriate for the baby care products 40 provided in the kit 10. For example, if a kit 10 contains a plurality of diapers 50 sized for a newborn, the kit 10 may be provided to the caregiver within proximity to the newborn's birth. Since a majority of mothers deliver within an institutional care facility (e.g., hospital, women's center, birthing center), a kit 10 containing newborn-sized diapers 50 may be provided to the mother, father, or other caregiver at some point during the mother's or baby's stay at the facility. The kit 10 may be provided to the caregiver at some time proximate to the birth of the baby.

EXAMPLE

A preferred self-contained baby care kit may be a newborn care kit with a case reusable as a photograph box. The case may comprise a case made from paperboard and having the dimensions of approximately 12.75"×9"×4.25" (length×width×depth). The case may be hexahedral with 5 rectangular faces—a bottom wall and four side walls. The sixth face may be a lid also made from paperboard and having the dimensions of approximately 13"×9.25"×2.25" (length×width×depth). The lid may have a top surface and four flanges that extending from downwardly from the top surface. In the closed position, the lid may engage the case such that the flanges overlap the sidewalls in a one-to-one relationship. The case and lid may be encircled with a paperboard overwrap that provides a handle along one face of the case. The case may be partitioned into two compartment of relatively equal volume by a divider. The divider may substantially span the entire width and depth of the case. The two resulting compartment may be sized to house two rows of typically-sized photographic snapshots (e.g., 4"×6" or 3.5"×5").

During the initial use of the case, one compartment may store a reusable container of approximately 80 wipes. A suitable container of wipes may be Pampers Lavender™ Baby Wipes available from The Procter & Gamble Company, Cincinnati, Ohio. During the initial use of the case, the other compartment may store a plurality of diapers. A suitable plurality of diapers may be a 20 count package of Pampers Newborn Swaddlers™ available from The Procter & Gamble Company, Cincinnati, Ohio. The case may contain an effective amount of decorative confetti, fluff, or packaging material so as to keep the diapers and wipes relatively immobilized and padded during transport and storage.

The case may further contain an envelope housing numerous educational inserts. One or more inserts may instruct the caregiver on the subsequent use of the case as a photograph box. The insert may describe how to orient the photographs within the compartment and may describe how to use the one or more indexing inserts and/or stages of baby development inserts as dividers for the photographs. One or more inserts may be indexing inserts allowing for customization by the caregiver. One or more inserts may be stages of baby development inserts. At least one insert may be devoted to each of the following stages of baby development: pre-locomotive, discovering, exploring, learning, and training. The case may contain an additional information insert in the form a post card that may be returned by the caregiver. The additional information insert may also provide a toll-free telephone number and/or a World Wide Web address by which additional information may be acquired. The case may contain a product information insert that describes the wipes and diapers enclosed within the case.

The case may be provided to a mother and/father of a newborn at some point in proximity to the mother's labor. The case may be provided during the mother's or newborn's stay at a birthing facility and may be provided at discharge from the facility.

All documents cited in the Detailed Description of the Invention are, in relevant part, incorporated herein by reference; the citation of any document is not to be considered as an n admission that it is prior art with respect to the present invention.

While particular embodiments and/or individual features of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of educating a caregiver about baby care and development, wherein said method comprises the steps of:
   a. preparing a self-contained baby care kit comprising
      i) a storage case including a divider, said storage case being configurable for an initial use of storing at least one baby care product and a subsequent use of storing at least one subsequent item, wherein the divider is adapted to be selectively positioned by the caregiver to optimize interior space of the storage container for the subsequent use of storing at least one subsequent item, wherein the at least one subsequent item comprises photographs, wherein the divider is adapted to selectively divide the interior space into at least two compartments, and wherein at least one of the at least two compartments has a width that corresponds with photographic print sizes,
      ii) at least one baby care product, and
      iii) at least one educational insert;
   b. providing said self-contained baby care kit to a caregiver within proximity of a birth of a baby, said baby receiving care from said caregiver;
   c. allowing the caregiver to use said self-contained baby care kit; and
   d. allowing the caregiver to customize the storage case for the subsequent use of storing at least one subsequent item.

2. The method of claim 1 wherein the at least one baby care product is selected from the group consisting of diapers, wipes, and combinations thereof.

3. The method of claim 1 wherein said self-contained baby care kit comprises sufficient quantity the baby care product to span a 24 hour period of use.

4. The method of claim 1 wherein the at least one educational insert is a subsequent use insert providing instruction to the caregiver on a secondary use of the storage case upon removal of the baby care product.

5. The method of claim 1 wherein the at least one educational insert is a stage of development insert providing instruction to the caregiver related to a stage of development for a baby.

6. The method of claim 5 wherein said instruction to the caregiver related to the stage of development is selected from the group consisting of developmental insights, care tips, feeding tips, health tips, interaction tips, practical tips, and combinations thereof.

7. The method of claim 6 wherein the stage of development is selected from the group consisting of newborn stage, pre-locomotive stage, crawling stage, exploring stage, a learning stage, a training stage, and combinations thereof.

8. The method of claim 1 wherein the step of providing said self-contained baby care kit to a earegiver is performed during a caregiver's stay at a birthing facility.

9. The method of claim 1 wherein the at least one educational insert is an additional information insert instructing the caregiver on a method to obtain additional baby care and development information.

10. The method of claim 1, wherein the at least one educational insert is constructed for use in physically separating and organizing photographs.

11. A method of educating a caregiver about baby care and development, wherein said method comprises the steps of:
    a. preparing a self-contained baby care kit comprising
       i) a storage case including a divider, said storage case being configurable for an initial use of storing at least one baby care product and a subsequent use of storing at least one baby-related memento, wherein the divider is adapted to be selectively positioned by the caregiver to optimize interior space of the storage container for the subsequent use of storing at least one baby-related memento, wherein the at least one baby-related memento comprises photographs, wherein the divider is adapted to selectively divide the interior space into at least two compartments, and wherein at least one of the at least two compartments has a width that corresponds with photographic print sizes,
       ii) a plurality of diapers,
       iii) a plurality of wipes, and
       iv) at least one educational insert;
    b. providing said self-contained baby care kit to a caregiver within proximity of a birth of a baby, said baby receiving care from said caregiver;
    c. instructing the caregiver as to a secondary use of the storage case;
    d. allowing the caregiver to interact with the at least one educational insert;
    e. allowing the caregiver to use said plurality of diapers and said plurality of wipes; and
    f. allowing the caregiver to customize the storage case for the subsequent use of storing at least one baby-related memento.

12. The method of claim 11 wherein the step of instructing the caregiver as to the secondary use of the storage case is performed by use of an educational insert comprising instructions regarding the secondary use.

13. The method of claim 11 wherein the step of allowing the caregiver to use said plurality of diapers and said plurality of wipes spans a period greater than 24 hours.

14. The method of claim 11 wherein the step of providing said self-contained baby care kit to a caregiver is performed during a caregiver's stay at a birthing facility.

15. The method of claim 11 wherein the at least one educational insert includes information selected from the group consisting of developmental insight, care tips, feeding tips, health tips, interaction tips, practical tips, and combinations thereof.

16. The method of claim 11 wherein the at least one educational insert includes information directed to a baby stage of development, said baby stage of development being selected from the group consisting of newborn stage, prelocomotive stage, crawling stage, exploring stage, a learning stage, a training stage, and combinations thereof.

17. The method of claim 11, wherein the at least one educational insert is constructed for use in physically separating and organizing photographs.

* * * * *

UNITED STATES PATENT AND TRADEMARK OFFICE
CERTIFICATE OF CORRECTION

| | | |
|---|---|---|
| PATENT NO. | : 7,491,062 B2 | Page 1 of 1 |
| APPLICATION NO. | : 10/918632 | |
| DATED | : February 17, 2009 | |
| INVENTOR(S) | : Mickey J. Suh et al. | |

It is certified that error appears in the above-identified patent and that said Letters Patent is hereby corrected as shown below:

<u>Col. 14; Claim 8</u>
Line 2, delete "earegiver" and insert -- caregiver --.

Signed and Sealed this

Twenty-second Day of September, 2009

David J. Kappos
*Director of the United States Patent and Trademark Office*